(12) United States Patent
Hu

(10) Patent No.: US 11,793,984 B2
(45) Date of Patent: Oct. 24, 2023

(54) VASCULAR ACCESS INSTRUMENT AND RELATED DEVICES AND METHODS

(71) Applicant: Becton, Dickinson and Company, Franklin Lakes, NJ (US)

(72) Inventor: Olivia Hu, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 176 days.

(21) Appl. No.: 17/357,515

(22) Filed: Jun. 24, 2021

(65) Prior Publication Data
US 2022/0016407 A1    Jan. 20, 2022

Related U.S. Application Data

(60) Provisional application No. 63/054,141, filed on Jul. 20, 2020.

(51) Int. Cl.
*A61B 5/15* (2006.01)
*A61M 25/00* (2006.01)
(Continued)

(52) U.S. Cl.
CPC ... *A61M 39/0247* (2013.01); *A61B 5/150992* (2013.01); *A61M 25/0097* (2013.01);
(Continued)

(58) Field of Classification Search
CPC ........ A61B 5/150992; A61M 25/0097; A61M 39/223; A61M 2039/0036;
(Continued)

(56) References Cited

U.S. PATENT DOCUMENTS 3,834,372 A * 9/1974 Turney ............... F16K 11/085
600/561
4,311,137 A    1/1982 Gerard
(Continued)

FOREIGN PATENT DOCUMENTS

KR    20180110514    10/2018
WO    2008/043034    4/2008
(Continued)

*Primary Examiner* — Katherine H Schwiker
*Assistant Examiner* — Robert F Allen
(74) *Attorney, Agent, or Firm* — KIRTON MCCONKIE; Whitney Blair; Kevin Stinger

(57) ABSTRACT

A vascular access system may include a catheter assembly, which may include a catheter hub and a catheter extending distally from the catheter hub. The vascular access system may include an instrument advancement device coupled to the catheter assembly. The instrument advancement device may include a vascular access instrument. The vascular access instrument may include a coil formed by a flat wire wound around an axis into multiple loops. The instrument advancement device may be configured to advance the vascular access instrument from a retracted position to an advanced position beyond a distal end of the catheter. The distal end of the catheter may include a distal opening. The coil may extend through the distal opening of the catheter in response to the vascular access instrument being in the advanced position.

11 Claims, 14 Drawing Sheets

(51) Int. Cl.
*A61M 39/22* (2006.01)
*A61M 39/10* (2006.01)
*A61M 39/00* (2006.01)
*A61M 39/20* (2006.01)
*A61M 39/02* (2006.01)
*A61M 25/06* (2006.01)

(52) U.S. Cl.
CPC .... *A61M 25/0618* (2013.01); *A61M 25/0693* (2013.01); *A61M 39/223* (2013.01); *A61M 2039/0036* (2013.01); *A61M 2039/0063* (2013.01); *A61M 2039/0258* (2013.01); *A61M 2039/0273* (2013.01); *A61M 2039/1072* (2013.01); *A61M 2039/1077* (2013.01); *A61M 2039/205* (2013.01); *A61M 2039/229* (2013.01)

(58) Field of Classification Search
CPC .. A61M 2039/0063; A61M 2039/0258; A61M 2039/1072; A61M 2039/1077; A61M 2039/205; A61M 2039/229; A61M 39/0247; A61M 2039/0273; A61M 25/0693

See application file for complete search history.

(56) References Cited

U.S. PATENT DOCUMENTS

| | | | |
|---|---|---|---|
| 5,496,301 A | * | 3/1996 | Hlavinka ............ B29C 66/8122 600/580 |
| 6,497,994 B1 | | 12/2002 | Kafrawy |
| 8,357,119 B2 | | 1/2013 | Stout et al. |
| 8,602,058 B1 | * | 12/2013 | Del Castillo ..... F16K 31/52466 251/227 |
| 2008/0287906 A1 | * | 11/2008 | Burkholz .......... A61M 25/0693 604/533 |
| 2011/0009717 A1 | * | 1/2011 | Davis ............... A61B 5/150992 600/573 |
| 2012/0232498 A1 | | 9/2012 | Ma et al. |
| 2013/0090607 A1 | | 4/2013 | McKinnon et al. |
| 2017/0120012 A1 | * | 5/2017 | Sonderegger ..... A61M 25/0637 |
| 2018/0353117 A1 | * | 12/2018 | Bullington .......... A61B 5/15003 |
| 2019/0247642 A1 | * | 8/2019 | Karthikeyan ...... A61M 39/1011 |
| 2020/0046948 A1 | * | 2/2020 | Burkholz ............ A61M 25/065 |
| 2021/0228121 A1 | * | 7/2021 | Burkholz ............. A61M 39/04 |
| 2021/0228126 A1 | * | 7/2021 | Naidu ............... A61M 25/0084 |

FOREIGN PATENT DOCUMENTS

| | | |
|---|---|---|
| WO | 2016/033143 | 3/2016 |
| WO | 2020/033137 | 2/2020 |

* cited by examiner

VASCULAR ACCESS INSTRUMENT AND RELATED DEVICES AND METHODS

RELATED APPLICATIONS

This application claims benefit of U.S. Provisional Patent Application No. 63/054,141, filed on Jul. 20, 2020, entitled VASCULAR ACCESS INSTRUMENT AND RELATED DEVICES AND METHODS, which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and the introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using the catheter may be difficult for several reasons, particularly when a dwell time of the catheter within the vasculature is more than one day. When the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, the catheter is often used for acquiring a blood sample at a time of catheter placement, but the catheter is less frequently used for acquiring a blood sample during the catheter dwell period. Therefore, when a blood sample is required, an additional needle stick is often used to provide vein access for blood collection, which may be painful for the patient and result in higher material costs.

In some instances, in order to avoid the additional needle stick, a vascular access instrument may be used to access the vasculature of the patient via the catheter. The vascular access instrument may be inserted through the catheter and into the vasculature to extend a life of the catheter and allow blood withdrawal through the catheter without the additional needle stick.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices, systems, and methods. More particularly, the present disclosure relates to a catheter system and related devices and methods. In some embodiments, a catheter system may include a catheter hub, which may include a distal end, a proximal end, a side port disposed between the distal end of the catheter hub and the proximal end of the catheter hub, and a lumen extending through the distal end of the catheter hub and the proximal end of the catheter hub. In some embodiments, the catheter system may include a catheter extending distally from the distal end of the catheter hub.

In some embodiments, the catheter system may include a Y-adapter, which may include a distal end, a first port, and a second port. In some embodiments, the catheter system may include an extension tube, which may include a distal end integrated with the side port and a proximal end integrated with the distal end of the Y-adapter. In some embodiments, the catheter system may include a septum disposed within the Y-adapter. In some embodiments, the septum may include a distal end, a proximal end, a lumen extending through the distal end of the septum, a side opening in fluid communication with the lumen of the septum, and a vent extending from the proximal end of the septum. In some embodiments, the septum may be movable between a prime position and an infusion position. In some embodiments, in response to the septum being in the prime position the vent may be aligned with the second port. In some embodiments, in response to the septum being in the infusion position, the side opening may be aligned with the second port.

In some embodiments, the septum may be coupled to a housing that extends out of the proximal end of the Y-adapter. In some embodiments, the Y-adapter may include a slot disposed around a portion of a circumference of the Y-adapter. In some embodiments, the slot may include a notch. In some embodiments, the housing may include a protrusion. In some embodiments, the protrusion may be disposed within the notch in response to the septum being in the prime position. In some embodiments, in response to the septum being moved from the prime position to the infusion position, the housing may be moved distally and the protrusion may slide along the slot.

In some embodiments, the lumen of the septum may be aligned with a longitudinal axis of the Y-adapter. In some embodiments, an outer surface of the proximal end of the septum may be non-circular and may correspond to a shape of an inner surface of the housing. In some embodiments, a length of the extension tube may be less than that of a BD NEXIVA™ Closed IV Catheter System or other catheter systems known in the art. In some embodiments, the length of the extension tube may be 1-4 inches, 1-3 inches, 1-2 inches, or another suitable length.

In some embodiments, the housing may be coupled to a needle assembly. In some embodiments, the needle assembly may include a body, a needle extending proximally from the body, and an elastomeric sheath coupled to the body and covering the needle. In some embodiments, the catheter system may include a blood collection tube holder coupled to the body of the needle assembly. In some embodiments, the body may be monolithically formed as a single unit with the housing.

In some embodiments, the catheter system may include a needle hub coupled to the proximal end of the catheter hub. In some embodiments, the needle hub may include a flashback chamber. In some embodiments, the catheter system may include an introducer needle extending distally from the needle hub and through the catheter.

In some embodiments, the catheter system may include another extension tube, which may include a distal end and a proximal end. In some embodiments, the distal end may be coupled to the second port of the Y-adapter. In some embodiments, the catheter system may include another Y-adapter coupled to the proximal end of the other extension tube. In some embodiments, the catheter system may include a needleless connector coupled to the second port.

In some embodiments, another septum may be disposed within the second port, and may be configured to pass air but not blood. In some embodiments, the needleless connector may be coupled to the second port of the Y-adapter. In some embodiments, the needleless connector may include a distal end and a proximal end, and the catheter system may include another extension tube coupled to the proximal end of the needleless access connector. In some embodiments, the catheter system may include another septum disposed within the first port of the Y-adapter. In some embodiments, the septum may be disposed in an open position in response to the needle assembly being coupled to the first port.

It is to be understood that both the foregoing general description and the following detailed description are examples and explanatory and are not restrictive of the present disclosure, as claimed. It should be understood that the various embodiments are not limited to the arrangements and vascular access instrumentality shown in the drawings. Also, the drawings are not necessarily to scale. It should also be understood that the embodiments may be combined. For example, one or more features of a particular vascular access instrument may be combined with one or more features of another particular vascular access instrument. It should also be understood that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
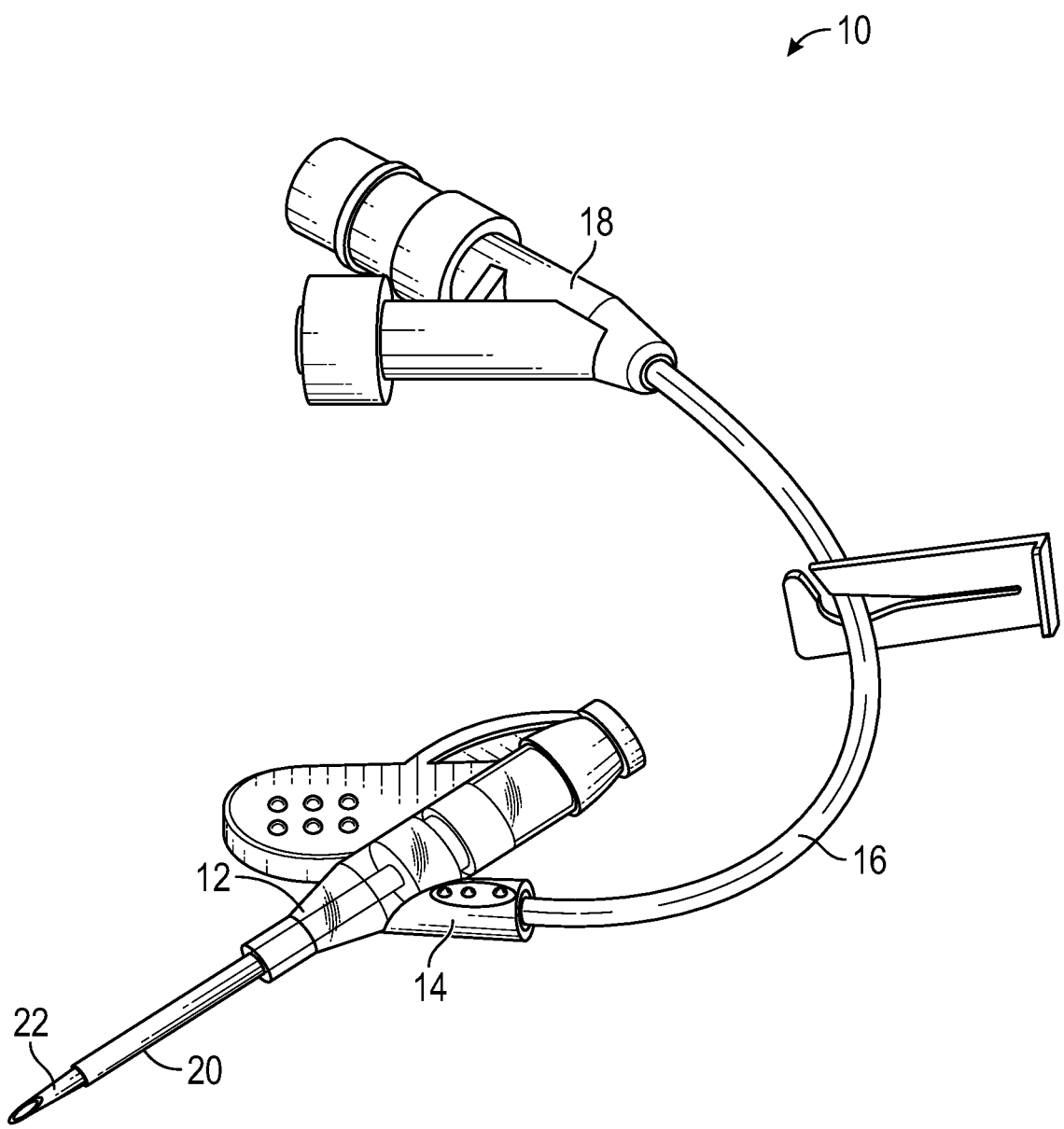
FIG. 1 is an upper perspective view of a prior art catheter system, according to some embodiments.
Figure 2:
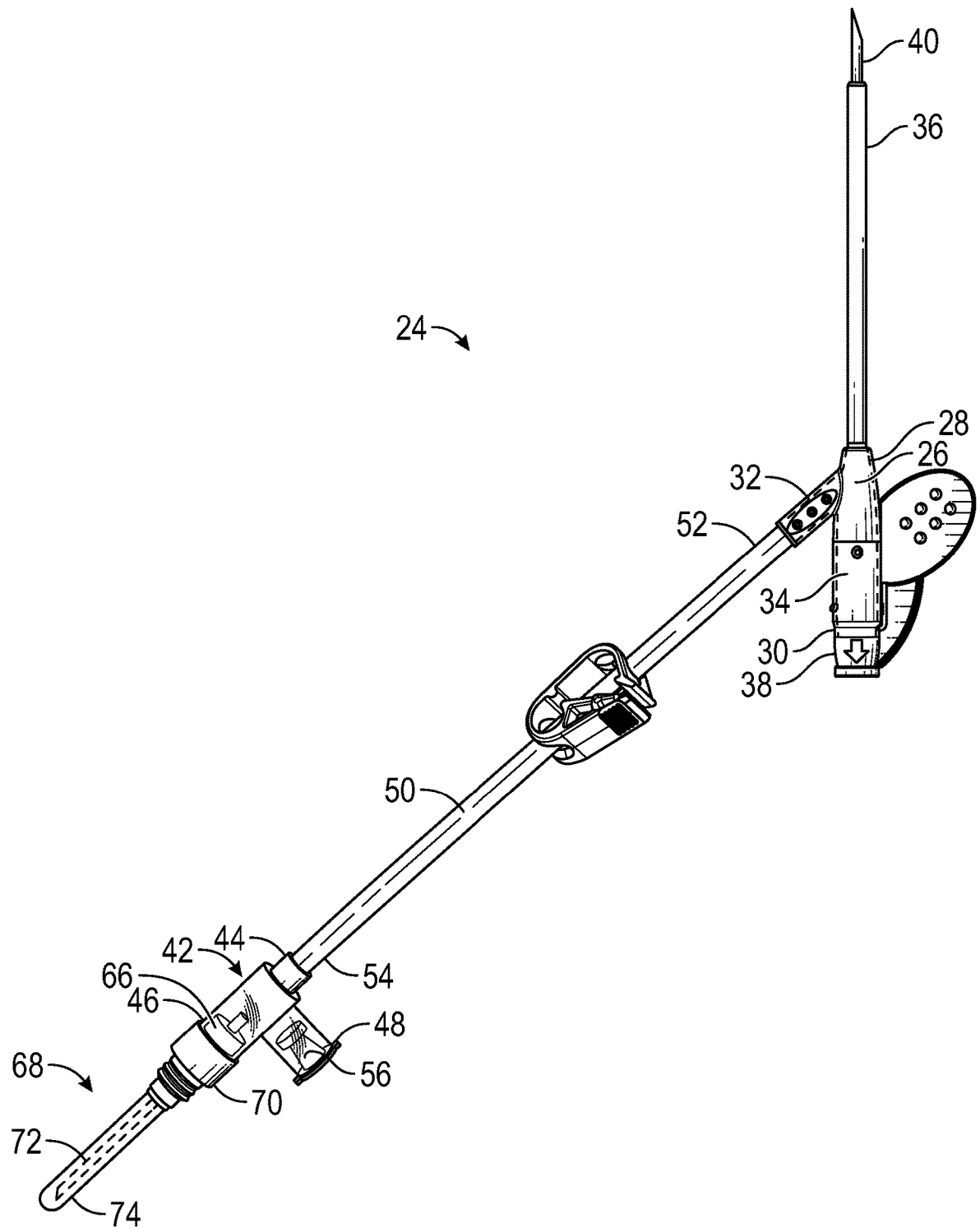
FIG. 2 is an upper perspective view of a catheter system, illustrating an example Y-adapter coupled to an example needle assembly, according to some embodiments.
Figure 3:
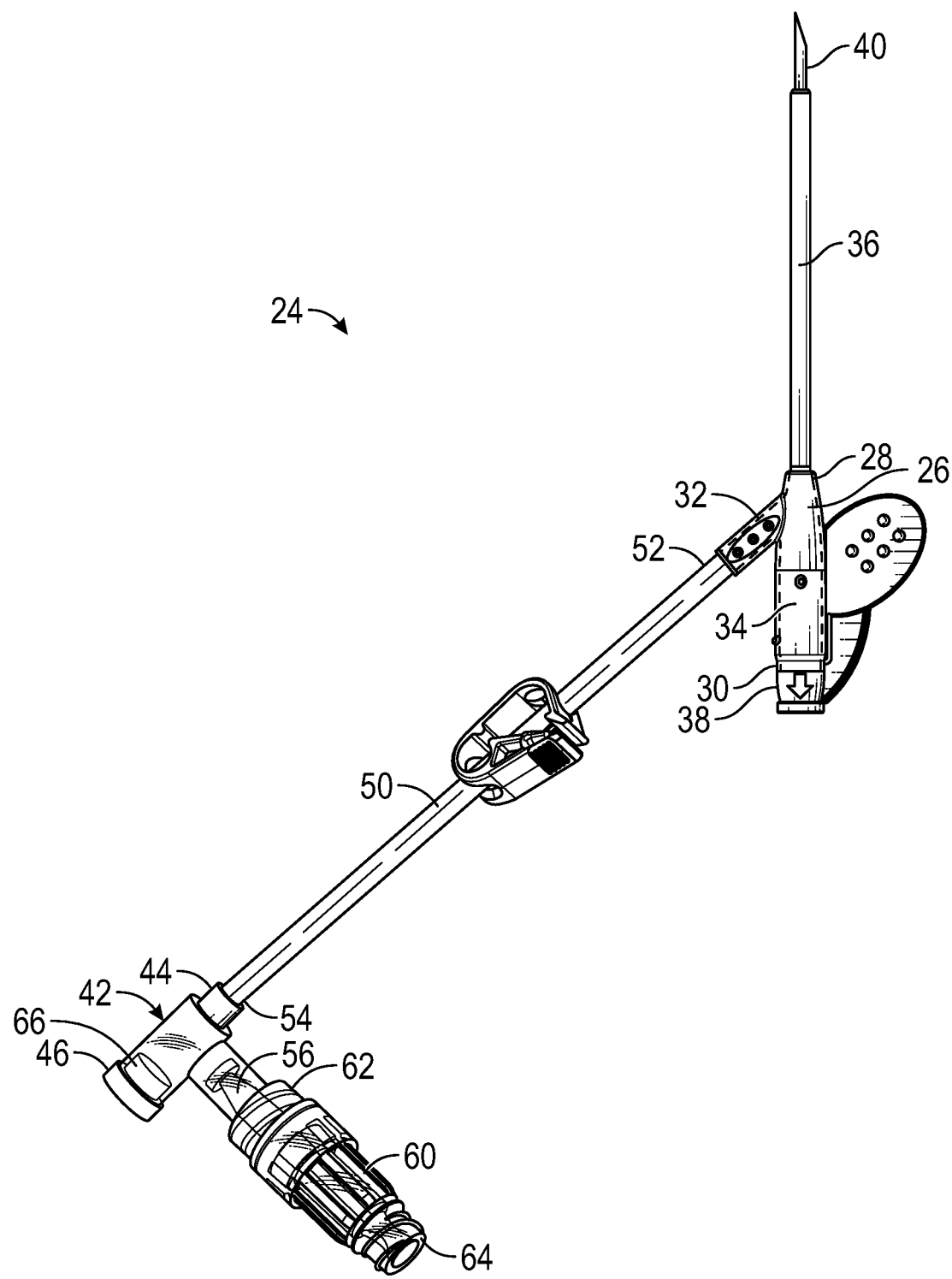
FIG. 3 is an upper perspective view of the catheter system of FIG. 2, illustrating the Y-adapter coupled to an example needleless connector, according to some embodiments.
Figure 4A:
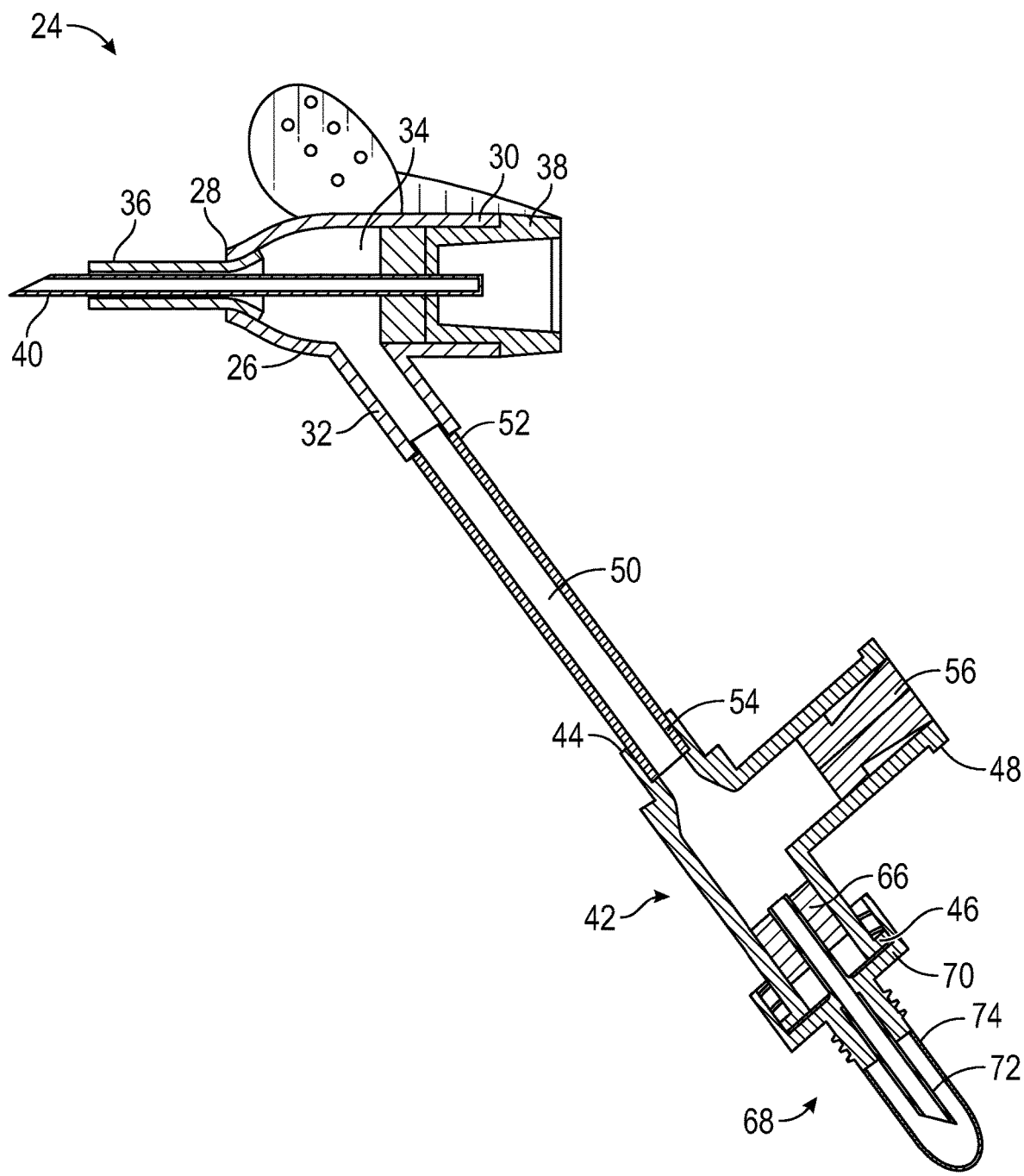
FIG. 4A is a cross-sectional view of the catheter system of FIG. 2, illustrating the Y-adapter coupled to the needle assembly, according to some embodiments.
Figure 4B:
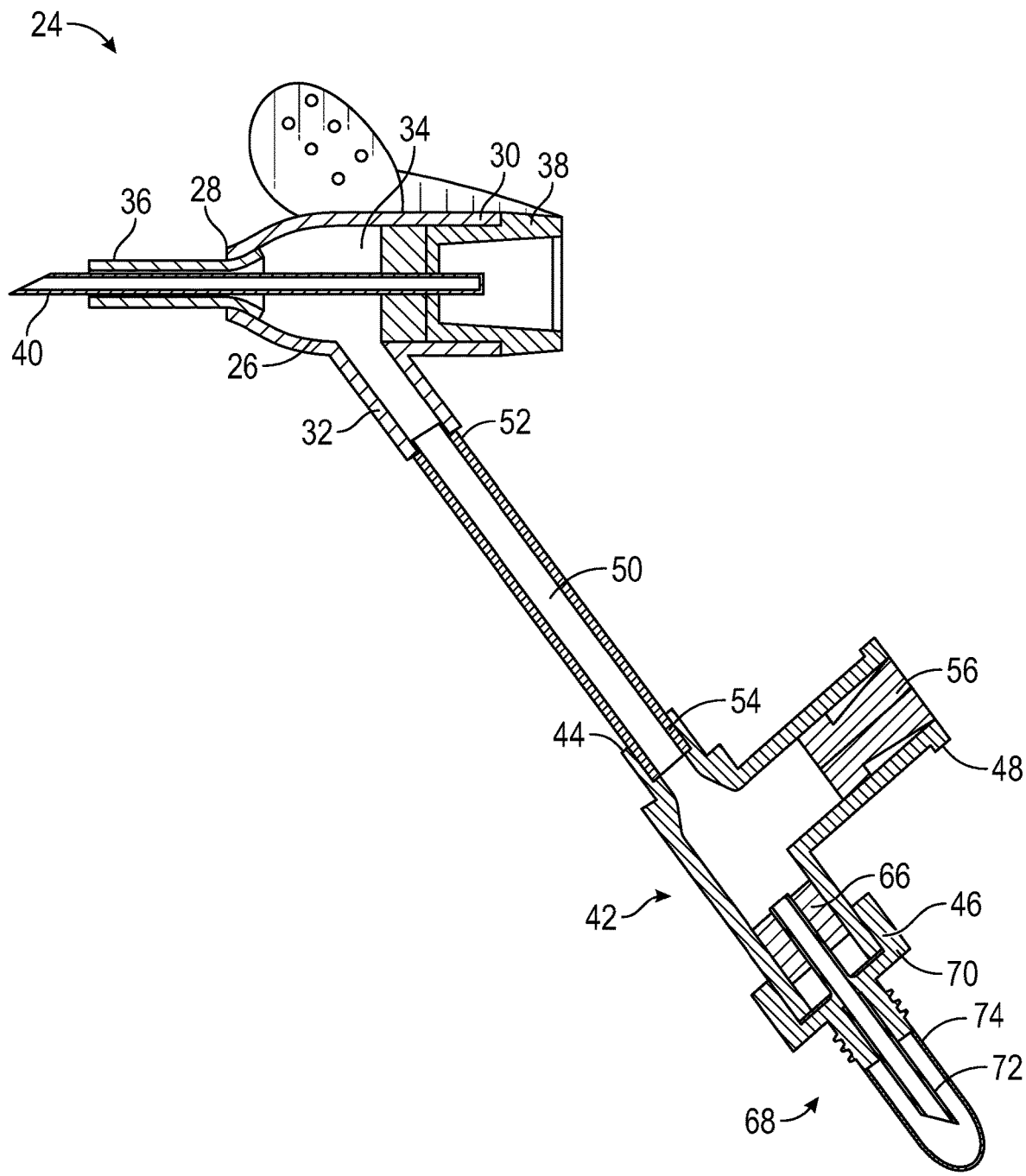
FIG. 4B is a cross-sectional view of the catheter system of FIG. 2, illustrating the Y-adapter coupled to the needle assembly and an example slip-fit, according to some embodiments.
Figure 4C:
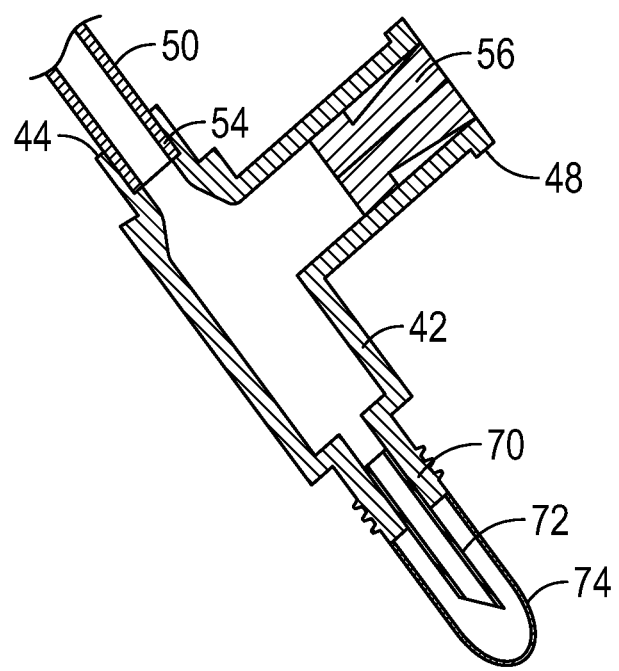
FIG. 4C is a cross-sectional view of a portion of the catheter system of FIG. 2, illustrating the Y-adapter monolithically formed as a single unit with the needle assembly, according to some embodiments.
Figure 5:
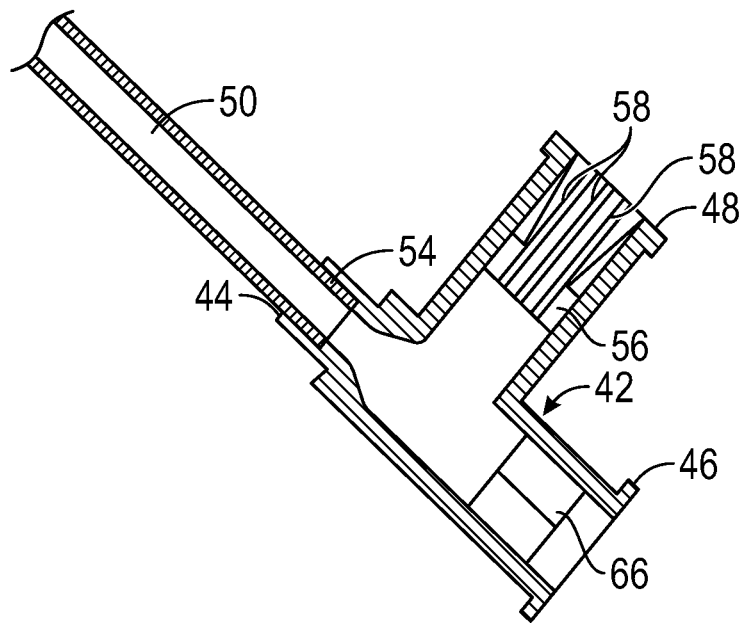
FIG. 5 is a partial cutaway view of the Y-adapter of the catheter system of FIG. 2, according to some embodiments.
Figure 6:
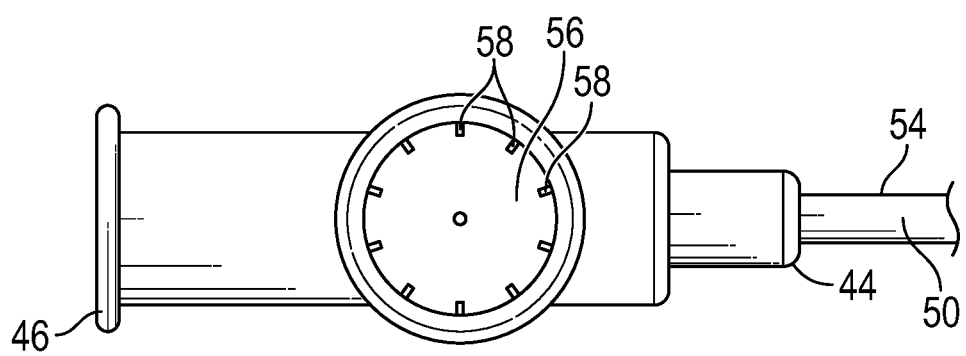
FIG. 6 is a side view of the Y-adapter of the catheter system of FIG. 2, according to some embodiments.

Referring now to FIG. 1, a prior art catheter system 10 is illustrated. The prior art catheter system 10 includes a catheter hub 12 with a side port 14 and a long extension tube 16 extending from the side port 14. A Y-adapter 18 is often disposed at a proximal end of the long extension tube 16. A catheter 20 may extend from the catheter hub 12 and may be inserted into vasculature of a patient via an introducer needle 22, which is removed from the prior art catheter system 10 after the catheter 20 is positioned within the vasculature. The prior art catheter system 10 with the catheter 20 positioned within the vasculature may be used for blood withdrawal or fluid infusion. The long extension tube 16 may create a tortuous blood flow path and lower blood pressure, slowing a blood collection time. Also, the Y-adapter 18 may retain blood or fluid and may not flush well.

Referring now to FIGS. 2-6, in some embodiments, a catheter system 24 may include a catheter hub 26, which may include a distal end 28, a proximal end 30, a side port 32 disposed between the distal end 28 of the catheter hub 26 and the proximal end 30 of the catheter hub 26, and a lumen 34 extending through the distal end 28 of the catheter hub 26 and the proximal end 30 of the catheter hub 26. In some embodiments, the catheter system 24 may include a catheter 36 extending distally from the distal end 28 of the catheter hub 26. In some embodiments, the catheter 36 may include a peripheral intravenous catheter, a peripherally-inserted central catheter, or a midline catheter. In some embodiments, a needle hub 38 may be removably coupled to the proximal end 30 of the catheter hub 26. In some embodiments, an introducer needle 40 may extend from the needle hub 38 and through the catheter 36 in an insertion position to insert the catheter system 24 into the vasculature of the patient.

In some embodiments, the catheter system 24 may include a Y-adapter 42, which may include a distal end 44, a first port 46, and a second port 48. In some embodiments, the first port 46 and/or the second port 48 may include a luer adapter, such as, for example, a female luer adapter. In some embodiments, the catheter system 24 may include an extension tube 50, which may include a distal end 52 integrated with the side port 32 and a proximal end 54 integrated with the distal end 44 of the Y-adapter 42. In some embodiments, a clamp may be disposed on the extension tube 50. In other embodiments, the extension tube 50 may not include the clamp.

In some embodiments, the Y-adapter 42 may reduce or eliminate dead space, where blood gets trapped during blood collection or fluid gets trapped during infusion. Further, the Y-adapter may provide air venting, which may facilitate blood collection. In some embodiments, a large angle between the first port 46 and the second port 48, such as, for example 90° or between 60° and 90°, may reduce the dead space. In some embodiments, a length of the first port 46 and/or the second port 48 may also be shortened to reduce the dead space. In some embodiments, the length of the first port 46 and/or the second port 48 may be 1-2 inches or another suitable length, which may reduce dead space and improve flushing.

In some embodiments, a septum 56 may be disposed within the second port 48, and may be configured to pass air but not fluid, such as blood. For example, an outer surface of the septum 56 may include one or more grooves 58 and/or an inner surface of the second port 48 may include one or more grooves. In some embodiments, dimensions of the grooves 58 and/or the grooves of the inner surface may allow air but not fluid to pass.

In some embodiments, a needleless connector 60 may be coupled to the second port 48 of the Y-adapter 42. In some embodiments, the needleless connector 60 may be coupled to the second port 48 after blood collection is complete. In some embodiments, the needleless connector 60 may include a first end 62 and a second end 64, and the catheter system 24 may include another extension tube coupled to the second end 64 of the needleless connector 60.

In some embodiments, the catheter system 24 may include another septum 66 disposed within the first port 46 of the Y-adapter 42. In some embodiments, the other septum 66 may be disposed in an open position in response to a needle assembly 68 being coupled to the first port 46, as illustrated, for example, in FIGS. 4A-4B. In some embodiments, the needle assembly 68 may include a body 70, a needle 72 extending proximally from the body 70, and an elastomeric sheath 74 coupled to the body 70 and covering the needle 72. In some embodiments, the needle assembly 68 may include a luer adapter, such as, for example, a male luer adapter, which may be coupled to the first port 46. In some embodiments, the luer adapter may be threaded (see, for example, FIG. 4A) or slip-fit (see, for example, FIG. 4B). In some embodiments, the needle assembly 68 may be pre-attached to the catheter system 24 in a kit. In some embodiments, the body 70 may be monolithically formed as a single unit with a housing, as illustrated, for example, in FIG. 4C. In some embodiments, the needle assembly 68 may be removed and replaced with a luer connector after blood collection is complete.

Figure 8:
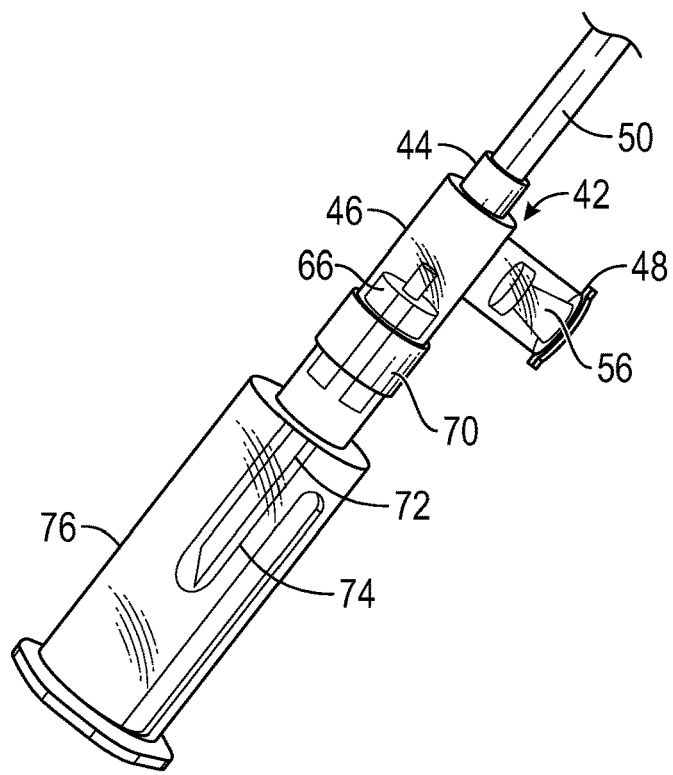
FIG. 8 is an upper perspective view of the Y-adapter of the catheter system of FIG. 2 coupled to an example blood collection tube, according to some embodiments.

In some embodiments, the catheter system 24 may include a blood collection tube holder 76 coupled to the body 70 of the needle assembly 68, as illustrated, for example, in FIG. 8. In some embodiments, the blood collection tube holder 76 may be coupled to the body 70 of the needle assembly 68 via one or more threads or another suitable means. In some embodiments, the blood collection tube holder 76 may be configured to receive a blood collection tube. In response to depression of the blood collection tube within the blood collection tube holder 76, the needle 72 communication between the catheter system 24 and the blood collection tube.

Figure 7:
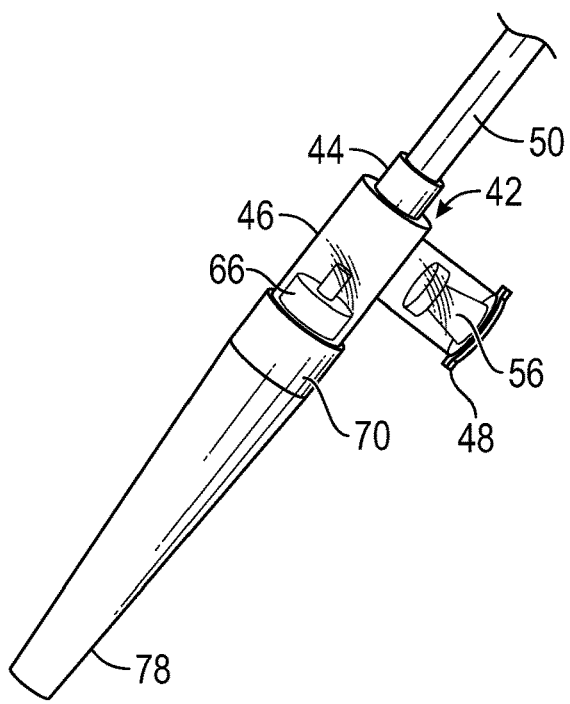
FIG. 7 is an upper perspective view of the Y-adapter of the catheter system of FIG. 2 coupled to an example cap, according to some embodiments.

In some embodiments, during blood collection, blood may flow proximally through the catheter 36, the catheter hub 26, the extension tube 50, the Y-adapter 42, and the needle assembly 68. In some embodiments, blood collection may be done at insertion of the catheter 36 into the vasculature and/or later on after the catheter 36 has been dwelling within the vasculature due to the septum 66 being accessed by the needle assembly 68. In some embodiments, the needleless connector 60 may prevent contamination prior to a later blood collection event after the catheter 36 has been inserted into the vasculature. In some embodiments, the needle assembly 68 further comprises a cap 78 disposed over the elastomeric sheath 74, as illustrated, for example, in FIG. 7, which may prevent contamination.

Figure 9:
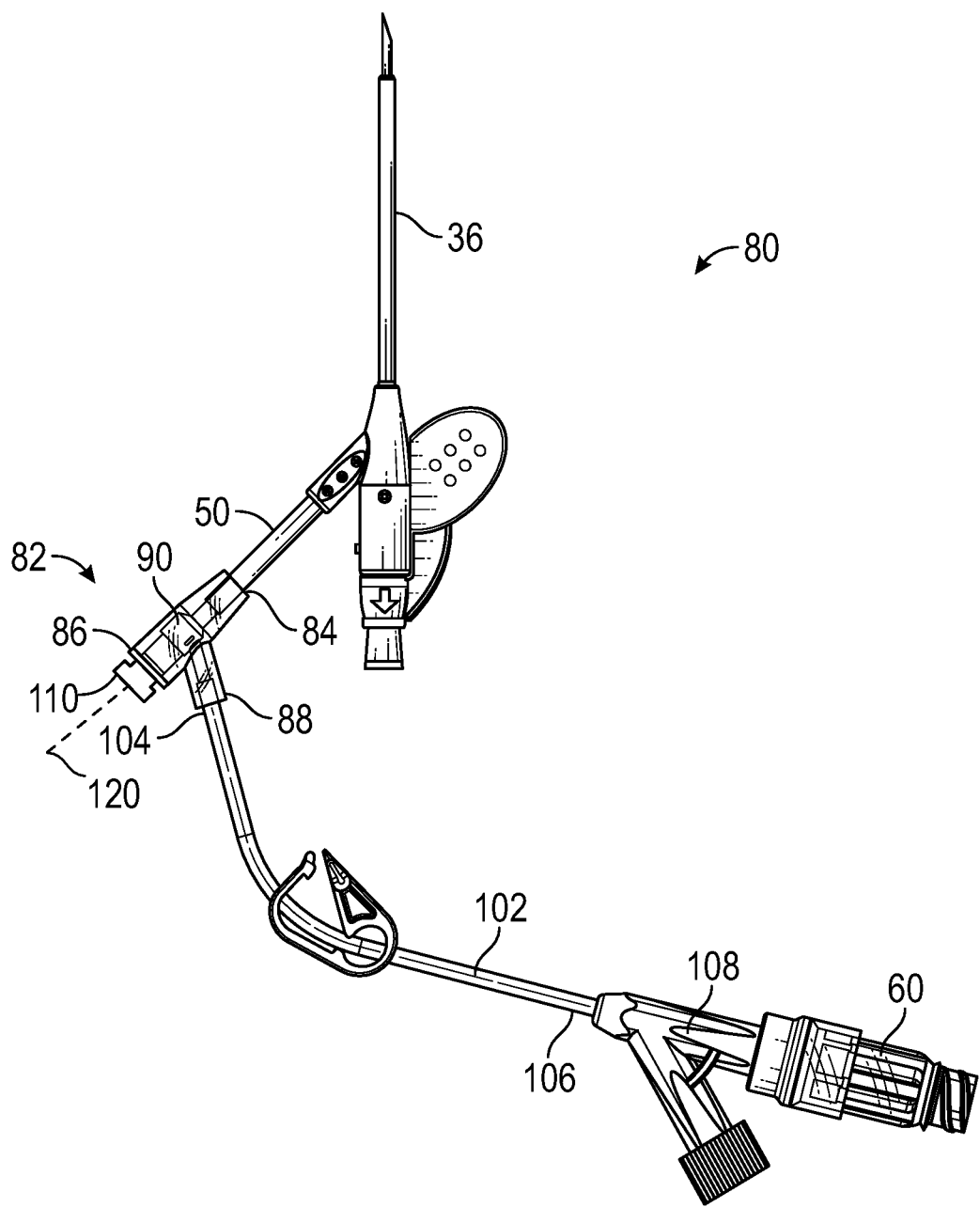
FIG. 9 is an upper perspective view of another catheter system, according to some embodiments.
Figure 10A:
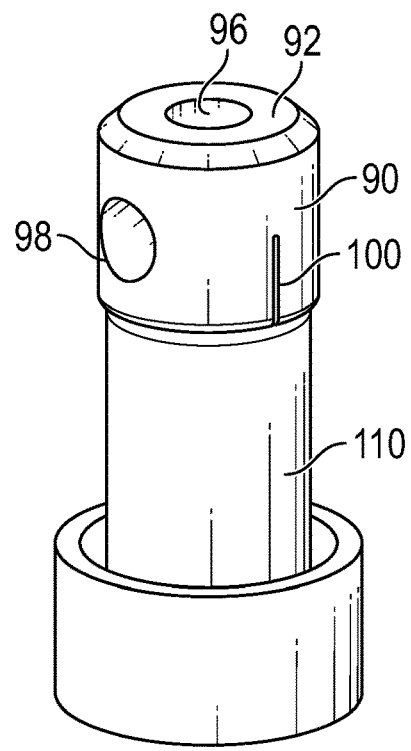
FIG. 10A is an upper perspective view of an example septum and example housing of the catheter system of FIG. 9, according to some embodiments.
Figure 10B:
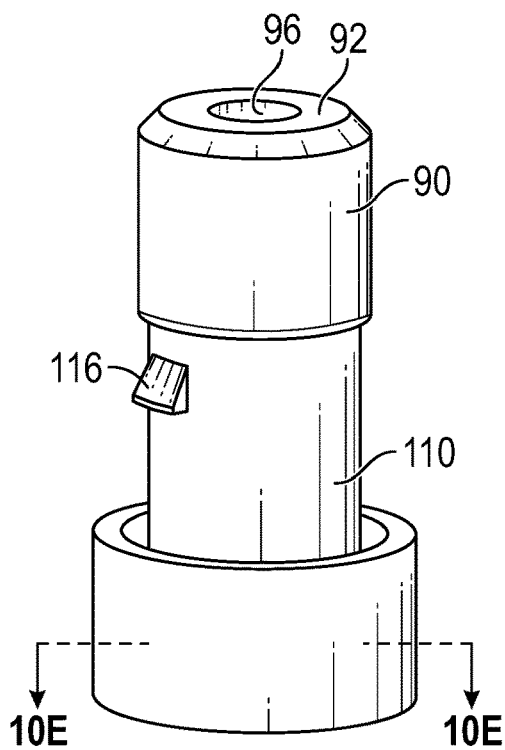
FIG. 10B is another upper perspective view of the septum and the housing of the catheter system of FIG. 9, according to some embodiments.
Figure 10C:
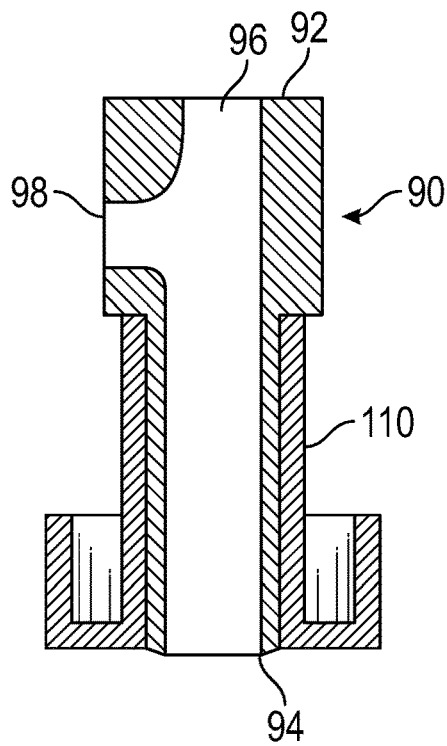
FIG. 10C is a cross-sectional view of the septum and the housing of the catheter system of FIG. 9, according to some embodiments.
Figure 10D:
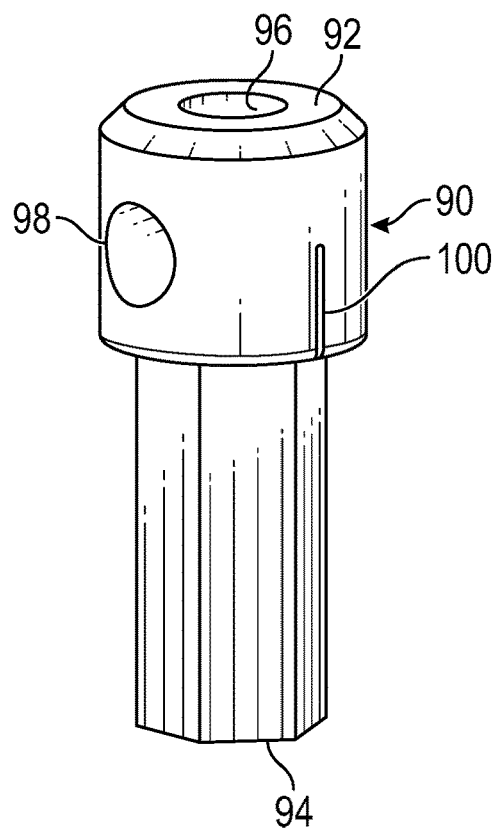
FIG. 10D is an upper perspective view of the septum of the catheter system of FIG. 9, according to some embodiments.
Figure 10E:
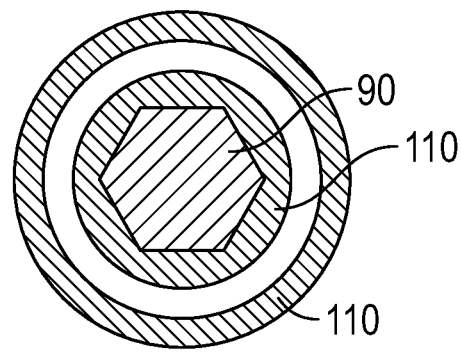
FIG. 10E is a transverse cross-sectional view of the septum and the housing of the catheter system of FIG. 9 along the line 10E-10E of FIG. 10B.
Figure 11A:
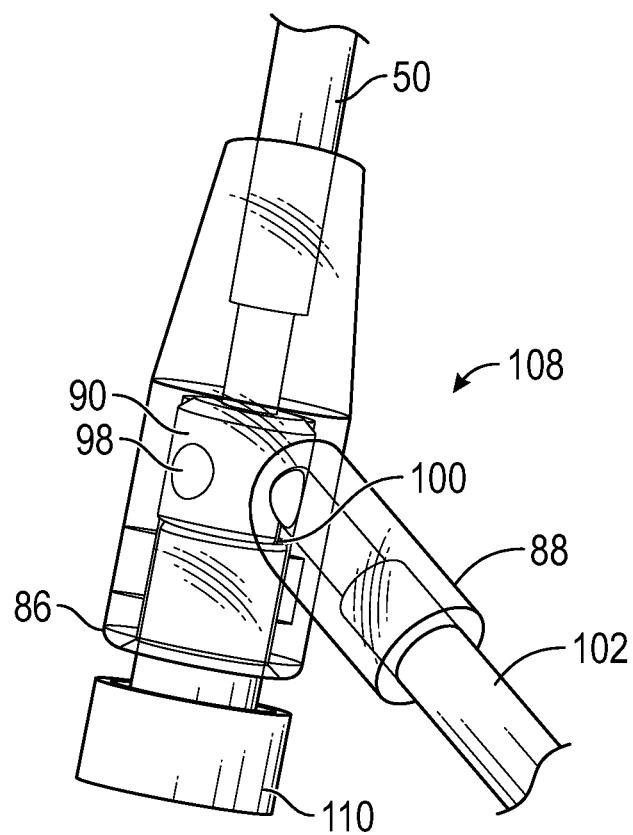
FIG. 11A is an upper perspective view is an upper perspective view of an example Y-adapter of the catheter system of FIG. 9, illustrating the septum in the prime position, according to some embodiments.
Figure 11B:
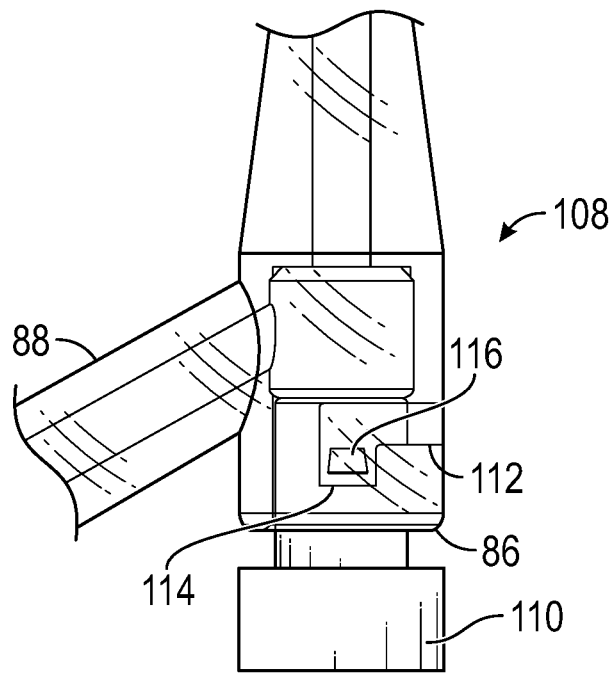
FIG. 11B is an upper perspective view is an upper perspective view of the Y-adapter of the catheter system of FIG. 9, illustrating the septum in the prime position, according to some embodiments.
Figure 11C:
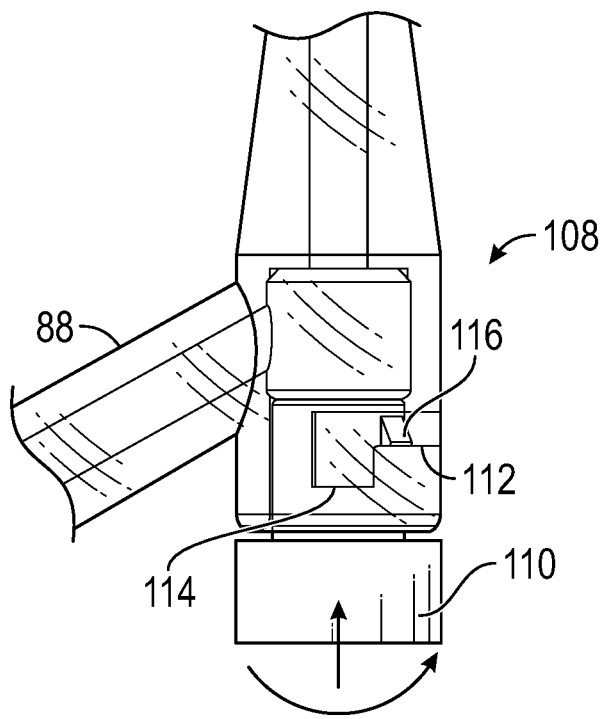
FIG. 11C is an upper perspective view is an upper perspective view of an example Y-adapter of the catheter system of FIG. 9, illustrating the septum in the prime position, according to some embodiments.
Figure 11D:
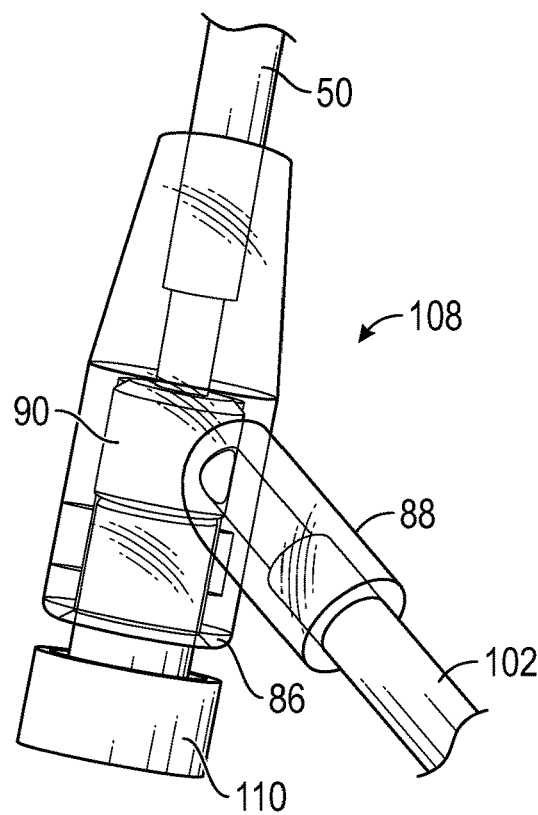
FIG. 11D is an upper perspective view of the Y-adapter of the catheter system of FIG. 9, illustrating the septum in an example infusion position, according to some embodiments.
Figure 11E:
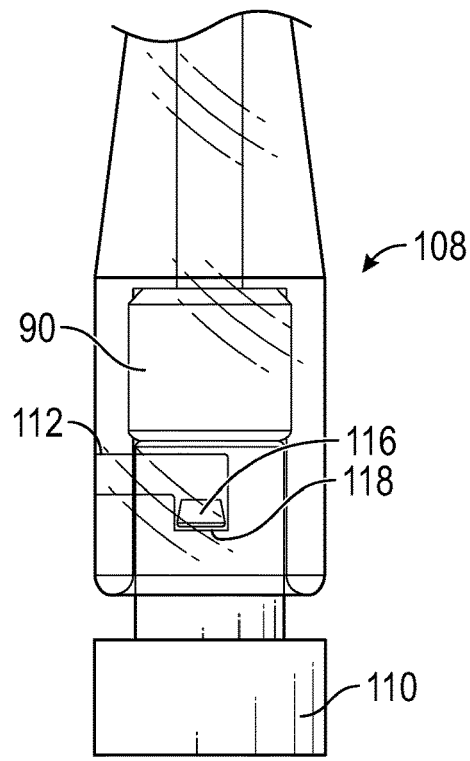
FIG. 11E is another upper perspective view is an upper perspective view of the Y-adapter of the catheter system of FIG. 9, illustrating the septum in the infusion position, according to some embodiments.

Referring now to FIGS. 9-11, a catheter system 80 may include the catheter hub 26, which may include the distal end 28, the proximal end 30, the side port 32 disposed between the distal end 28 of the catheter hub 26 and the proximal end 30 of the catheter hub 26, and the lumen 34 extending through the distal end 28 of the catheter hub 26 and the proximal end 30 of the catheter hub 26. In some embodiments, the catheter system 24 may include the catheter 36 extending distally from the distal end 28 of the catheter hub 26. In some embodiments, the catheter 36 may include a peripheral intravenous catheter, a peripherally-inserted central catheter, or a midline catheter. In some embodiments, the catheter system 80 may be similar or identical to the catheter system 24 in terms of one or more included features and/or operation.

In some embodiments, the needle hub 38 may be removably coupled to the proximal end 30 of the catheter hub 26. In some embodiments, the introducer needle 40 may extend from the needle hub 38 and through the catheter 36 in the insertion position to insert the catheter system 24 into the vasculature of the patient.

In some embodiments, the catheter system 80 may include a Y-adapter 82, which may include a distal end 84, a first port 86, and a second port 88. In some embodiments, the first port 86 and/or the second port 88 may include a luer adapter, such as, for example, a female luer adapter. In some embodiments, the catheter system 80 may include the extension tube 50, which may include the distal end 52 integrated with the side port 32 and the proximal end 54 integrated with the distal end 84 of the Y-adapter 82. In some embodiments, a clamp may be disposed on the extension tube 50. In other embodiments, the extension tube 50 may not include the clamp.

In some embodiments, the Y-adapter 82 may include a septum 90 disposed within the Y-adapter 82. In some embodiments, the septum 90 may include one or more of the following: a distal end 92, a proximal end 94, a lumen 96 extending through the distal end 92 of the septum 90, a side opening 98 in fluid communication with the lumen 96 of the septum 90, and a vent 100 extending from the proximal end 94 of the septum 90. In some embodiments, the septum 90 may be movable between a prime position, illustrated, for example, in FIGS. 11A-11B, and an infusion position, illustrated, for example, in FIGS. 11D-11E. In some embodiments, in response to the septum 90 being in the prime position, the vent 100 may be aligned with the second port 88.

In some embodiments, the catheter system 80 may include another extension tube 102, which may include a distal end 104 and a proximal end 106. In some embodiments, the distal end 104 may be coupled to the second port 88 of the Y-adapter 82. In some embodiments, the catheter system 80 may include another Y-adapter 108 coupled to the proximal end 106 of the other extension tube 102. In some embodiments, the catheter system 80 may include the needleless connector 60 coupled to the second port 88. In some embodiments, one or more of the following: the other extension tube 102, the other Y-adapter 108, and the needleless connector 60 may be primed with a priming solution, such as, for example, saline, when the septum 90 is in the prime position. In some embodiments, the vent 100 may facilitate movement of air from the other extension tube 102 to an external environment. In some embodiments, in response to the septum 90 being in the prime position, air may flow through the vent 100 and into the external environment. In some embodiments, the vent 100 may extend proximal to a proximal end 106 of the Y-adapter 82 or there may be a small space between an inner surface of the Y-adapter 82 and an outer surface of the septum 90 proximal to the vent 100, and the small space may allow air to pass to the external environment.

In some embodiments, in response to the septum 90 being in the infusion position, the side opening 98 may be aligned with the second port 88. Thus, fluid may flow from the other. extension tube 102 through the side opening 98, out the distal end 92 of the septum 90, through the extension tube 50, and through the catheter hub 26 and the catheter 36 into the vasculature of the patient.

In some embodiments, the septum 90 may be coupled to a housing 110 that extends out of the proximal end of the Y-adapter 82. In some embodiments, the Y-adapter 82 may include a slot 112 disposed around a portion of a circumference of the Y-adapter 82. In some embodiments, the slot 112 may include a notch 114. In some embodiments, the housing 110 may include a protrusion 116. In some embodiments, the protrusion 116 may be disposed within the notch 114 in response to the septum 90 being in the prime position. In some embodiments, the of the septum 90 in response to movement of the housing 110.

In some embodiments, the slot 112 may include another notch 118. In some embodiments, the notch 114 and the other notch 118 may be disposed at opposing ends of the slot 112. In some embodiments, in response to the septum 90 being moved from the prime position to the infusion position, the housing 110 may be moved distally and the protrusion 116 may slide along the slot 112. In some embodiments, the protrusion 116 may be disposed within the other notch 118 in response to the septum 90 being in the infusion position.

In some embodiments, the lumen 96 of the septum 90 may be aligned with a longitudinal axis 120 of the Y-adapter. In some embodiments, an outer surface of the proximal end 94 of the septum 90 may be non-circular and may correspond to a shape of an inner surface of the housing 110.

In some embodiments, the housing 110 may be coupled to the needle assembly 68. In some embodiments, the needle assembly 68 may include the body 70, the needle 72 extending proximally from the body 70, and the elastomeric sheath 74 coupled to the body 70 and covering the needle 72. In some embodiments, the catheter system 80 may include the blood collection tube holder coupled to the body of the needle assembly 68, as illustrated, for example, in FIG. 8. In some embodiments, the body 70 may be monolithically formed as a single unit with the housing 110.

In some embodiments, the catheter system 80 may include the needle hub 38 coupled to the proximal end 30 of the catheter hub 26. In some embodiments, the needle hub 38 may include a flashback chamber. In some embodiments, the catheter system 24 may include the introducer needle 40 extending distally from the needle hub 38 and through the catheter 20.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

We claim:

1. A catheter system, comprising:
   a catheter hub, comprising a distal end, a proximal end, a side port disposed between the distal end of the catheter hub and the proximal end of the catheter hub, and a lumen extending through the distal end of the catheter hub and the proximal end of the catheter hub;
   a catheter extending distally from the distal end of the catheter hub;
   a Y-adapter, comprising a distal end, a first port, and a second port;
   an extension tube, comprising a distal end integrated with the side port and a proximal end integrated with the distal end of the Y-adapter;
   a septum disposed within the Y-adapter, wherein the septum comprises a distal end, a proximal end, a lumen extending through the distal end of the septum, a side opening in fluid communication with the lumen of the septum, and a vent extending from the proximal end of the septum, wherein the septum is movable between a prime position and an infusion position, wherein in response to the septum being in the prime position the vent is aligned with the second port, wherein in response to the septum being in the infusion position, the side opening is aligned with the second port; and
   a housing, wherein the septum is coupled to the housing that extends out of a proximal end of the Y-adapter, wherein the Y-adapter further comprises a slot disposed around a portion of a circumference of the Y-adapter, wherein the slot comprises a notch, wherein the housing comprises a protrusion, wherein the protrusion is disposed within the notch in response to the septum being in the prime position, wherein in response to the septum being moved from the prime position to the infusion position, the housing is moved distally and the protrusion slides along the slot.

2. The catheter system of claim 1, wherein an outer surface of the proximal end of the septum is non-circular and corresponds to a shape of an inner surface of the housing.

3. The catheter system of claim 1, wherein the housing is coupled to a needle assembly, wherein the needle assembly comprises a body, a needle extending proximally from the body, and an elastomeric sheath coupled to the body and covering the needle.

4. The catheter system of claim 3, further comprising a blood collection tube holder coupled to the body of the needle assembly.

5. The catheter system of claim 3, wherein the body is monolithically formed as a single unit with the housing.

6. The catheter system of claim 1, further comprising:
a needle hub coupled to the proximal end of the catheter hub, wherein the needle hub comprises a flashback chamber; and
an introducer needle extending distally from the needle hub and through the catheter.

7. The catheter system of claim 1, further comprising:
a second extension tube, comprising a distal end and a proximal end, wherein the distal end of the second extension tube is coupled to the second port of the Y-adapter; and
another Y-adapter is coupled to the proximal end of the second extension tube.

8. The catheter system of claim 1, further comprising a needleless connector coupled to the second port.

9. The catheter system of claim 1, wherein the lumen of the septum is aligned with a longitudinal axis of the Y-adapter.

10. The catheter system of claim 1, wherein the distal end of the septum comprises a larger diameter than the proximal end of the septum and the septum comprises a stepped surface.

11. The catheter system of claim 10, wherein the vent is linear and extends proximally to the stepped surface, wherein a distal end of the housing contacts the stepped surface.

* * * * *